(12) United States Patent
Zelenchuk

(10) Patent No.: US 8,311,607 B2
(45) Date of Patent: *Nov. 13, 2012

(54) FLUORESCENT FIBEROPTIC PROBE FOR TISSUE HEALTH DISCRIMINATION AND METHOD OF USE THEREOF

(75) Inventor: Alex R. Zelenchuk, Stoughton, MA (US)

(73) Assignee: Luma Imaging Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/215,096

(22) Filed: Aug. 22, 2011

(65) Prior Publication Data

US 2012/0046554 A1    Feb. 23, 2012

Related U.S. Application Data

(63) Continuation of application No. 11/955,165, filed on Dec. 12, 2007, now Pat. No. 8,005,527, which is a continuation of application No. 10/894,356, filed on Jul. 19, 2004, now Pat. No. 7,310,547, which is a continuation of application No. 10/192,836, filed on Jul. 10, 2002, now Pat. No. 6,768,918.

(51) Int. Cl.
*A61B 5/00* (2006.01)

(52) U.S. Cl. .................. 600/407; 600/477; 600/478

(58) Field of Classification Search .................. 600/407, 600/473, 475–478; 436/63, 64, 172
See application file for complete search history.

(56) References Cited

U.S. PATENT DOCUMENTS

| | | | | |
|---|---|---|---|---|
| 5,421,339 | A * | 6/1995 | Ramanujam et al. | 600/477 |
| 6,091,985 | A * | 7/2000 | Alfano et al. | 600/476 |
| 6,258,576 | B1 * | 7/2001 | Richards-Kortum et al. | 435/40.52 |
| 6,768,918 | B2 * | 7/2004 | Zelenchuk | 600/476 |
| 7,310,547 | B2 * | 12/2007 | Zelenchuk | 600/407 |
| 8,005,527 | B2 * | 8/2011 | Zelenchuk | 600/407 |

* cited by examiner

*Primary Examiner* — Ruth S Smith
(74) *Attorney, Agent, or Firm* — Mintz, Levin, Cohn, Ferris, Golovsky and Popeo, P.C.

(57) ABSTRACT

A system and method for the in situ discrimination of healthy and diseased tissue. A fiberoptic based probe is employed to direct ultraviolet illumination onto a tissue specimen and to collect the fluorescent response radiation. The response radiation is observed at three selected wavelengths, one of which corresponds to an isosbestic point. In one example, the isosbestic point occurs at about 431 nm. The intensities of the observed signals are normalized using the 431 nm intensity. A score is determined using the ratios in a discriminant analysis. The tissue under examination is resected or not, based on the diagnosis of disease or health, according to the outcome of the discriminant analysis.

17 Claims, 4 Drawing Sheets

FLUORESCENT FIBEROPTIC PROBE FOR TISSUE HEALTH DISCRIMINATION AND METHOD OF USE THEREOF

REFERENCE TO PRIORITY DOCUMENTS

This application is a continuation of U.S. application Ser. No. 11/955,165, filed Dec. 12, 2007, now U.S. Pat. No. 8,005,527, issued Aug. 23, 2011, which is a continuation of U.S. application Ser. No. 10/894,356, filed Jul. 19, 2004, now U.S. Pat. No. 7,310,547, issued Dec. 18, 2007, which is a continuation of U.S. application Ser. No. 10/192,836, filed Jul. 10, 2002, now U.S. Pat. No. 6,768,918, issued Jul. 27, 2004. The disclosures of U.S. Pat. No. 8,005,527, U.S. Pat. No. 7,310,547, and U.S. Pat. No. 6,768,918 are incorporated herein by reference in their entirety.

GOVERNMENT RIGHTS

This invention was made with government support under a Small Business Innovation Research Grant (Contact #1R43CA75773-01) awarded by the Department of Health and Human Services. The government may have certain rights in the invention.

FIELD

This invention relates generally to diagnosis of disease. More particularly, the invention relates to in vivo diagnosis by optical methods.

BACKGROUND

Colonic polyps appear as two major types, neoplastic and non-neoplastic. Non-neoplastic polyps are benign with no direct malignant potential and do not necessarily need to be resected. Hyperplastic polyps, juvenile polyps, mucosal prolapse and normal mucosal polyps are examples of non-neoplastic polyps. Conversely, neoplastic polyps are pre-malignant, a condition requiring resection and further surveillance. Examples of premalignant neoplastic polyps are tubular adenoma, villous adenoma and tubulovillous adenoma.

Conventional laser-induced fluorescence emission and reflectance spectroscopy can distinguish between neoplastic and non-neoplastic tissue with accuracies approaching about 85%. However, typically these methods require that the full spectrum be measured with algorithms dependent on many emission wavelengths.

SUMMARY

The invention provides in vivo diagnostic methods based upon the normalized intensity of light emitted from tissue. In particular, it is an observation of the invention that relevant diagnostic information is provided by comparing the intensities of light emitted from a tissue at two different wavelengths, both normalized over the intensity of light emitted from the same tissue at about 431 nm.

Thus, according to the invention, a comparison of the intensities of two different wavelengths normalized using the intensity at about 431 nm provides diagnostic insight. Preferred methods of the invention comprise obtaining a fluorescent emission having a first intensity at a first wavelength and a second intensity at a wavelength; normalizing the first and second intensities with respect to an intensity at a wavelength of about 431 nm to produce first and second normalized intensities; and determining a state of health of the tissue based upon a comparison of the first and second normalized intensities.

In one embodiment, methods of the invention comprise determining the state of health of the tissue using a classifier function in which the first and second normalized intensities are inputs. In one embodiment, the classifier function is a discrimination function, preferably a linear discrimination function. In other embodiments, the discrimination function is a non-linear discrimination function.

The invention can be applied to analyze a broad range of tissues. Preferably, the tissue to be analyzed is a tissue comprising epithelial cells. In one embodiment, the tissue is selected from the group consisting of cervical tissue, colonic tissue, esophogeal tissue, bladder tissue, and bronchial tissue.

Classifying or comparing normalized intensities into one or more groups may be performed by any, acceptable means. There are numerous acceptable approaches to such classifications. For example, one general method of grouping the two normalized intensities is a Bayesian-based classifier using Mahalanobis distances. The Mahalanobis distance is well-known in statistical analysis, and is used to measure a distance between data in a multidimensional space based on characteristics that represent a degree of relationship among the data. Bayesian probabilities have been known in statistical analysis for many years. Specific Bayesian Mahalanobis-based classifier can be selected from linear discriminant analysis, quadratic discriminant analysis, and regularized discriminant analysis. As those familiar with statistical analysis will recognize, linear discrimination analysis and quadratic discriminant analysis are methods that are computationally efficient. Regularized discriminant analysis uses a biasing method based on two parameters to estimate class covariance matrices.

Other ways of comparing the normalized intensities include a binary tree classifier, and an unsupervised learning cluster classifier. Unsupervised learning is characterized by the absence of explicit examples showing what an input/output relation should be. Examples of an unsupervised learning cluster classifier include hierarchical clustering analysis, principal component analysis, fuzzy c-means analysis, and fuzzy k-means analysis. Each of the forgoing analytical techniques is well known in the statistical analysis literature. For example, the fuzzy c-means algorithm divides a data set having an integer number n data points into an integer number c fuzzy clusters, where n>c, while determining a location for each cluster in a multi-dimensional space.

In another aspect, the invention features systems for determining the state of health of a tissue. Systems of the invention comprise an illumination source for illuminating a tissue; a detector for receiving from the tissue light comprising a first intensity at a first wavelength and a second intensity, at a second wavelength; a computational module for normalizing the first and second intensities with respect to received light having an intensity at a wavelength of about 431 nm to produce first and second normalized intensities; and an analysis module for determining a state of health of the tissue based upon a comparison of the first and second normalized intensities.

In a preferred embodiment, a system of the invention comprises an optical fiber as the illumination source. The detector may receive light from the tissue by way of a plurality of optical fibers. In a preferred embodiment, at least one of the optical fibers of the system is placed directly in contact with tissue. Preferably, the light received from the tissue is fluorescent light. The analysis module of a system of the invention may comprise a Bayesian Mahalanobis-based classifier function. The Bayesian Mahalanobis-based classifier may be selected from the group consisting of linear discriminant analysis, quadratic discriminant analysis, and regularized discriminant analysis. The analysis module may also comprise a binary tree classifier function or an unsupervised learning cluster classifier. In some embodiments, the unsupervised learning cluster classifier is selected from the group consisting of hierarchical clustering analysis, principal component analysis, fuzzy c-means analysis, and fuzzy k-means analysis.

Systems and methods of the invention are useful in examining a tissue comprising epithelial cells. A method of the invention comprises laser-induced fluorescence using light around 337 nm and a threshold classification model that depends on two fluorescence intensity ratios normalized by the intensity of fluorescence at about 431 nm.

The invention enables determining whether a polyp is neoplastic. Systems and methods of the invention enable such determination at the time of endoscopy particularly for diminutive polyps. In a preferred embodiment, the invention provides for identification of polyps (or other features) under about 10 mm in size. In a further preferred embodiment, the invention provides for identification of polyps (or other features) under about 10 mm in size in real time.

The combination of a new design of a fiberoptic probe for making measurements, an analytic method based on a small number of data points, and a simple method of obtaining a normalization factor for the data used provides enhanced diagnostic accuracy in distinguishing between neoplastic and non-neoplastic polyps.

The invention provides methods that reliably distinguish between neoplastic and non-neoplastic tissue at the time of endoscopy, colonoscopy, colposcopy, or other similar examinations. As a result, patients with non-neoplastic lesions are not subjected to the risk, discomfort and expense of biopsies or excisions. Patients with neoplastic lesions can be identified immediately and treated.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below. The drawings are not necessarily to scale, emphasis instead generally being placed upon illustrating the principles of the invention. In the drawings, like numerals are used to indicate like parts throughout the various views.

DETAILED DESCRIPTION

Figure 1:
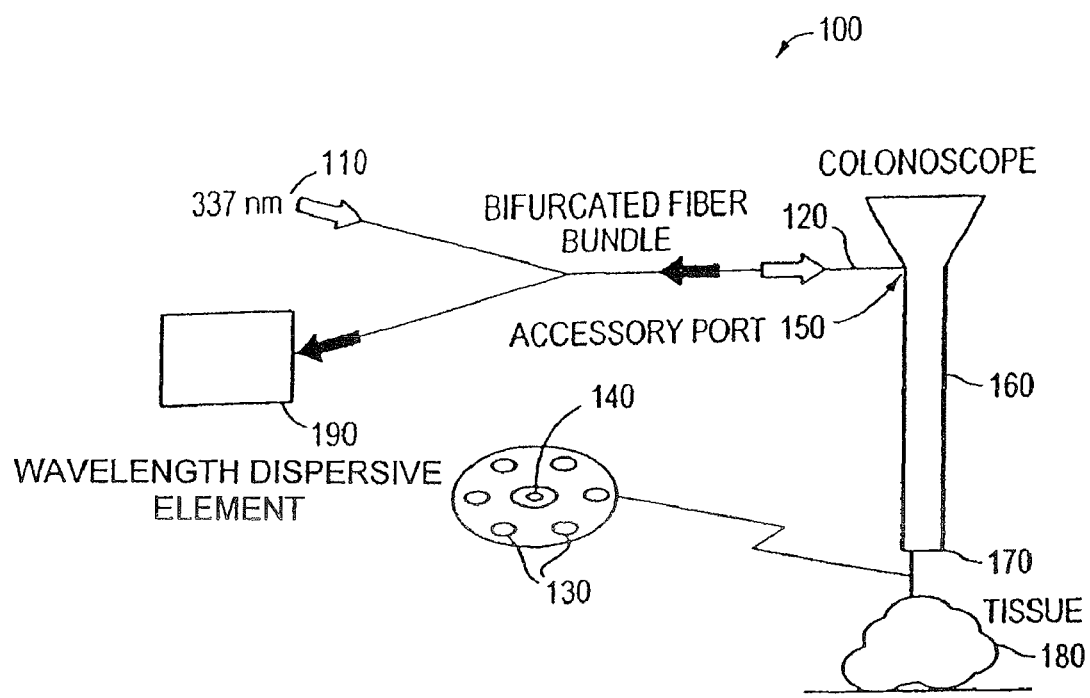
FIG. 1 is a schematic diagram showing an embodiment of the apparatus according to principles of the invention.

In one aspect, the invention utilizes the intensity of fluorescence observed at an isosbestic-like point as a point for normalization. An isosbestic point is a point in wavelength space (or its equivalent) at which a multi-component system exhibits a constant absorbance independent of the relative proportions of the components. Following normalization to peak fluorescence intensity, polyp fluorescence spectra exhibits nearly constant fluorescence intensities at 431 nm. A preferred isosbestic-like point for use in methods of the invention is 431 nm.

According to the invention, normalizing polyp fluorescence spectra to an isosbestic point is nearly equivalent to normalizing to their peak intensities. Generally, the invention involves illuminating a specimen and observing the intensity of responsive light at each of first and second wavelengths. These intensities are normalized with respect to the intensity of light at an isosbestic point. Normalized intensities are typically obtained by dividing an intensity of responsive light at a wavelength by the intensity of light at the isosbestic wavelength. In a preferred embodiment, the fluorescence isosbestic point occurs at a wavelength of about 431 nm.

The first and second wavelengths may be conveniently selected in accordance with a discrimination function analysis, which is described below in greater detail. The normalized responses are used at input values for the discrimination function analysis. The output of the discrimination function analysis is an indication that the specimen examined is healthy or is diseased.

The discrimination analysis can be linear or nonlinear. In general terms, the discrimination function is a mathematical relationship that is constructed in at least two-dimensional space. The mathematical relationship is constructed in relation to groupings of observations corresponding to one or more known medical conditions as compared to observations corresponding to another known condition (e.g., healthy). The discrimination function used in methods of the invention is a mathematical representation of one or more boundaries that separate observations obtained from the sample being interrogated from those corresponding to one or more groups associated with a known condition. As is appreciated by the skilled artisan, numerous discrimination techniques are available for application of the invention. Numerous such techniques are discussed below.

Example 1

In one embodiment, the invention is practiced by illuminating tissue with 337 nm excitation light delivered via a single optical fiber. Light that is remitted is collected with a plurality of optical fibers surrounding the illumination fiber. In one embodiment, signals from the individual collection fibers can be averaged into a single spectrum thereby increasing sensitivity. In an alternative embodiment, the signals from the individual collection fibers can be analyzed as discrete signals, for example, by comparing the different signal to determine an extent of tissue that provides a particular response.

An exemplary apparatus 100 used in this embodiment of the invention is shown in FIG. 1. The apparatus 100 includes a source 110 of 337 nm illumination as the excitation source. The excitation illumination is introduced into an optical fiber 120 for delivery to the tissue under examination. The illumination fiber 120 can be tapered starting at about 0.4 mm in diameter at the proximal end and ending at about 0.1 mm at its distal end. In one embodiment, a plurality of optical fibers 130 are used to collect the response signal from the tissue under examination. In the embodiment shown, six collection fibers 130 are placed in a hexagonal array about the central optical fiber 120 that carries the excitation illumination. This geometry is termed herein the "six-around-one fiberoptic probe." In alternative embodiments, additional hexagonal layers of fibers disposed so as to surround the collection fibers 130. The collection fibers are about 0.1 mm in diameter. The fiberoptic catheter 140 is delivered through the accessory port 150 of a typical endoscope 160 with the distal tip 170 gently touching tissue 180 to be examined. In one embodiment, the returned light is separated into fluorescence bands at 403, 414 and 431 nm using a wavelength dispersive element 190 such as a spectrograph or dichroic filter system. The width of the bands should preferably be under 5 nm. Two intensity ratios ($I_{403}/I_{431}$) and $I_{414}/I_{431}$) are then formed and used as input values in a linear discriminant analysis (LDA) threshold model to produce a score indicative of the health of the tissue. Treatment or further diagnostic procedures are based on a characteristic of the score, such as its sign.

This invention, in one embodiment, relates to an optical probe and methods for identifying neoplastic tissues of the colon during endoscopy or colonoscopy and of the cervix of the uterus during colposcopy as well as cancerous and/or pre-cancerous lesions of other organs, such as the esophagus, the urinary bladder, the oral cavity, and the bronchotracheal tree. Systems and methods of the invention can be usefully employed in examining a tissue comprising epithelial cells. A probe according to the invention comprises a plurality of collection fibers surrounding a single illumination fiber. Preferably, the plurality of collection fibers is six fibers. In a preferred embodiment, at least one of the optical fibers of the probe is placed directly in contact with tissue. A method of the invention comprises laser induced fluorescence using 337 nm excitation and a threshold classification model that depends on two fluorescence intensity ratios normalized by the intensity of fluorescence at about 431 nm. In a preferred embodiment, the intensity at about 403 nm is divided by the intensity at about 431 nm and the intensity at about 414 nm is divided by the intensity at 431 nm.

The invention enables determining whether a polyp is neoplastic. Systems and methods of the invention enable such determination at the time of endoscopy particularly for diminutive polyps. In an exemplary embodiment, fluorescent intensity at frequencies other than about 403 nm and about 414 nm are observed, and are normalized by dividing by the intensity of fluorescence observed at about 431 nm.

In a preferred embodiment, the invention provides for identification of polyps (or other features) under about 10 mm in size. In a further preferred embodiment, the invention provides for identification of polyps (or other features) under about 10 mm in size in real time.

Figure 2:
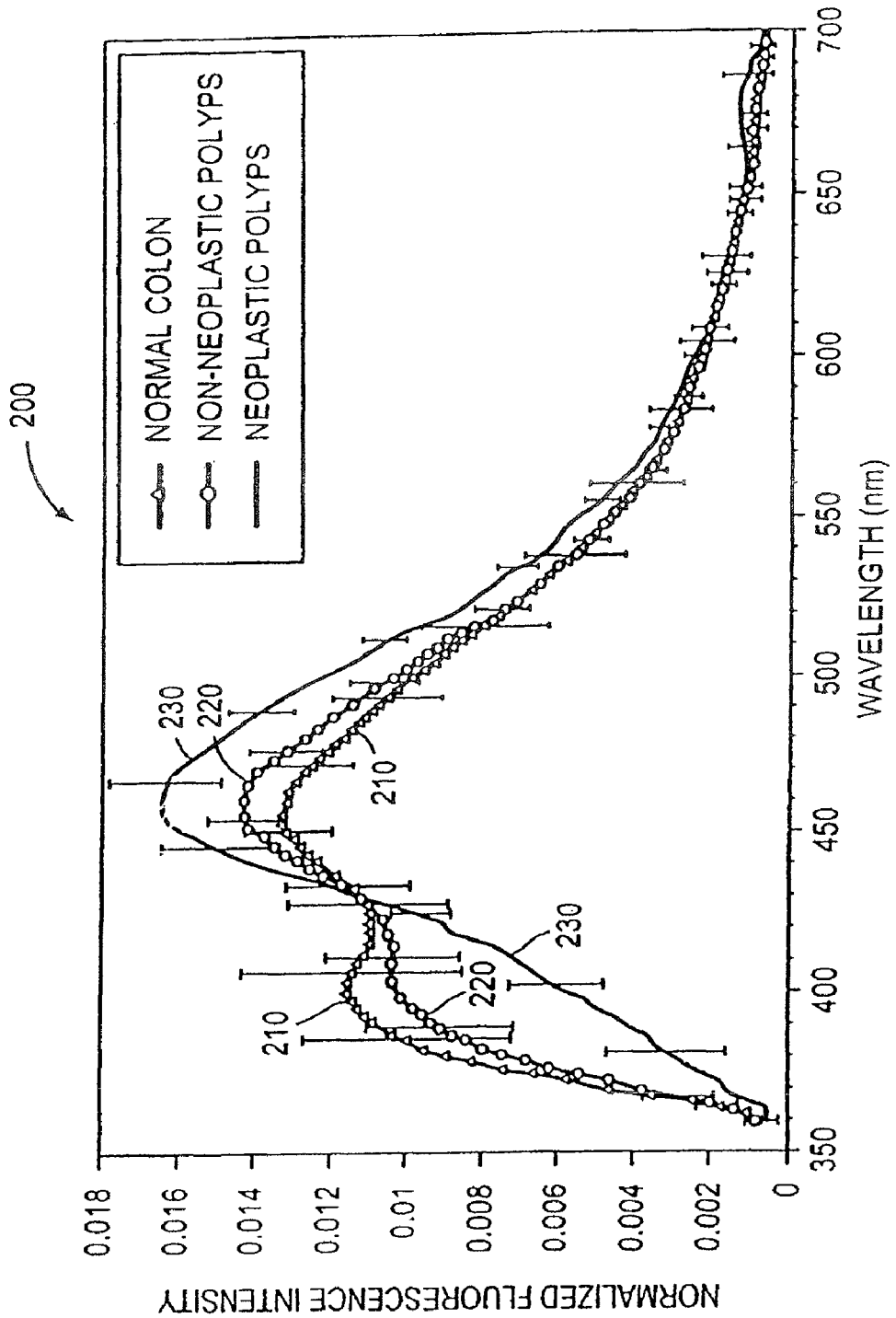
FIG. 2 is a plot of the normalized fluorescence spectra of normal colon, neoplastic polyps and non-neoplastic polyps showing a quasi-isosbestic point at 431 nm, according to an embodiment of the invention.

Referring to FIG. 2, a plot 200 depicting a plurality of response spectra is shown, for different tissue types illuminated with the same 337 nm excitation-light. In the example shown, the spectra observed correspond to tissues including normal colon 210, non-neoplastic polyps 220, and neoplastic polyps 230. There is a quasi-isosbestic point at 431 nm. The spectra 210, 220, 230 shown in FIG. 2 were recorded with the six-around-one fiberoptic probe.

Changes in optical properties of collagen and blood are the predominant factors in diagnostic differentiation among normal tissue, non-neoplastic polyps, and neoplastic polyps. An algorithm that treats collagen fluorescence, having a peak at about 403 nm in the system of the invention, and hemoglobin absorption, having a peak at about 414 nm for oxyhemoglobin, is sensitive to these changes.

Collagen and blood reside underneath the superficial cellular layer. A fiberoptic geometry designed to probe deeper into tissue but not too deep is more sensitive to changes in collagen and blood and hence in differentiating between types of polyps. The six-around-one fiberoptic probe used according to principles of the invention probes deeper into tissue than does a single fiber system.

Interpatient variability in the intensity of fluorescent response is typically large and affects the diagnostic accuracy of techniques based on absolute fluorescence intensities. Historically, effective diagnostic algorithms have used some form of normalization to reduce interpatient variability. One common approach that has been used is to preprocess the data by normalizing the area under each fluorescence spectrum to unity. However, this approach requires that the entire fluorescence spectrum be measured to calculate the area to be used for the normalization factor. The necessity to record an entire spectral response simply to be able to obtain normalization data is redundant and inefficient. The inefficiency is particularly acute if only the emissions at 1 or 2 wavelengths are to be analyzed.

According to the invention, a quasi-isosbestic point exists at about 431 nm between the fluorescence spectra of normal tissue, hyperplastic polyps and adenomatous polyps. The quasi-isosbestic point is used as a normalization factor that provides effective normalization while requiring fluorescence to be measured at only one addition emission wavelength. For other types of precancerous and/or cancerous polyps, other chemical substances are involved in the progress of the disease. These chemical substances provide characteristic signals that can occur at wavelengths other than at about 403 nm and about 414 nm.

The combination of a new design of a fiberoptic probe for making measurements, an analytic method based on a small number of data points, and a simple method of obtaining a normalization factor for the data used provides enhanced diagnostic accuracy in distinguishing between neoplastic and non-neoplastic polyps. The efficacy of the new system and method is demonstrated in a single-center prospective clinical trial. A higher fraction of polyps were correctly classified with this technique, (e.g., accuracy=86%) when compared to other approaches. The accuracy of the method using two emission wavelengths is better than that obtained in retrospective clinical trials requiring many more wavelengths. A retrospective trial is one in which one determines the sensitivity of an algorithm that was retrospectively optimized with data in hand. A prospective trial is one that uses a retrospectively trained algorithm in a prospective analysis of data collected after the algorithm is defined and tested.

Analysis Method

Figure 3:
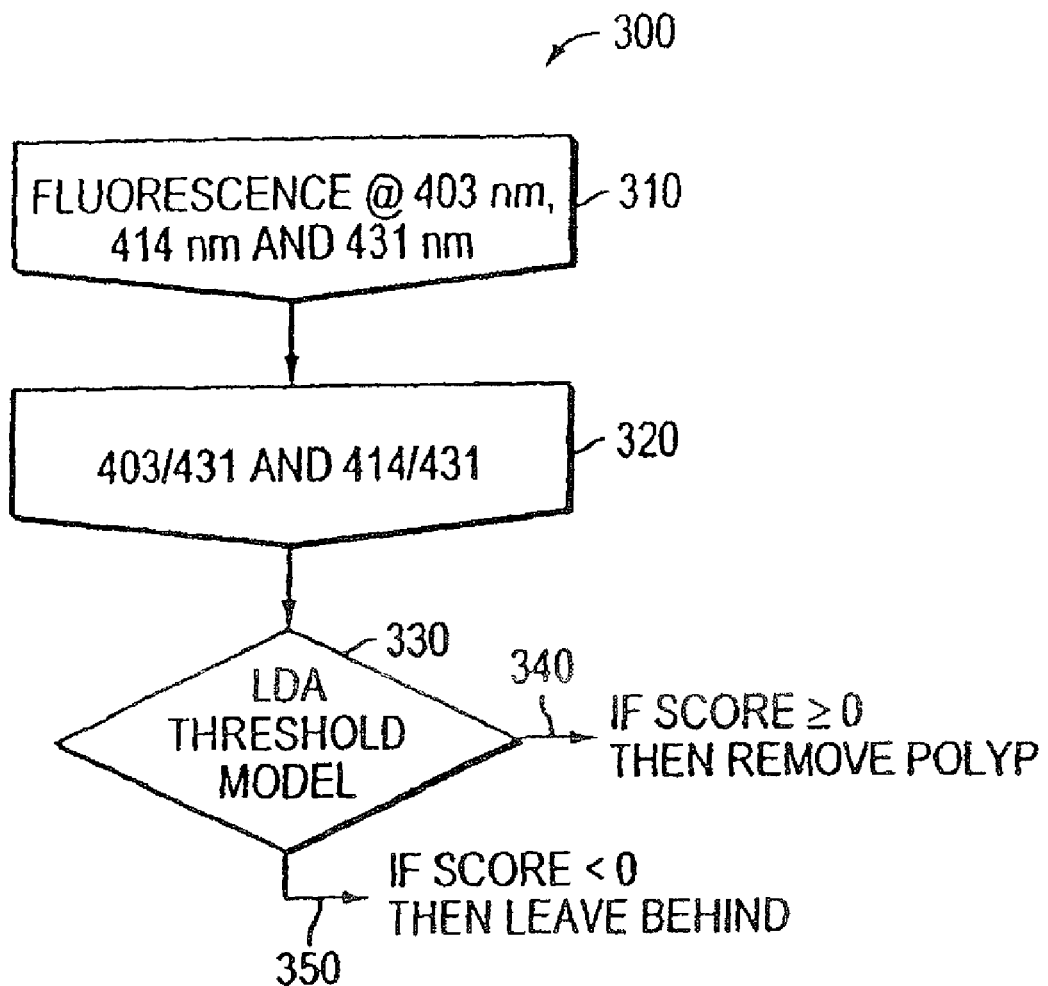
FIG. 3 is a flow diagram showing the steps of the analytical method according to principles of the invention.

FIG. 3 is a flow diagram 300 showing the steps of an illustrative analytical method as applied to the optical signals observed from colonic polyps. The method involves, in the example provided above, observing fluorescent intensities at about 403, about 414 and about 431 nm, as shown at step 310. The ratio of the intensity at about 403 nm to that at about 431 nm ($I_{403}/I_{431}$), and the ratio of the intensity at about 414 nm to that at about 431 nm ($I_{414}/I_{431}$) are formed, as indicated at step 320. The two ratios are then examined by comparison to a linear discrimination function, using linear discrimination analysis (LDA), as shown at step 330. A score value greater than zero is indicative of neoplasia, while a score value less than zero indicates non-neoplasia. Resection can be performed, or omitted, based on the score value that is obtained. Result 340 represents performing resection, while result 350 represents not performing resection.

Sensitivity Analysis

Figure 4:
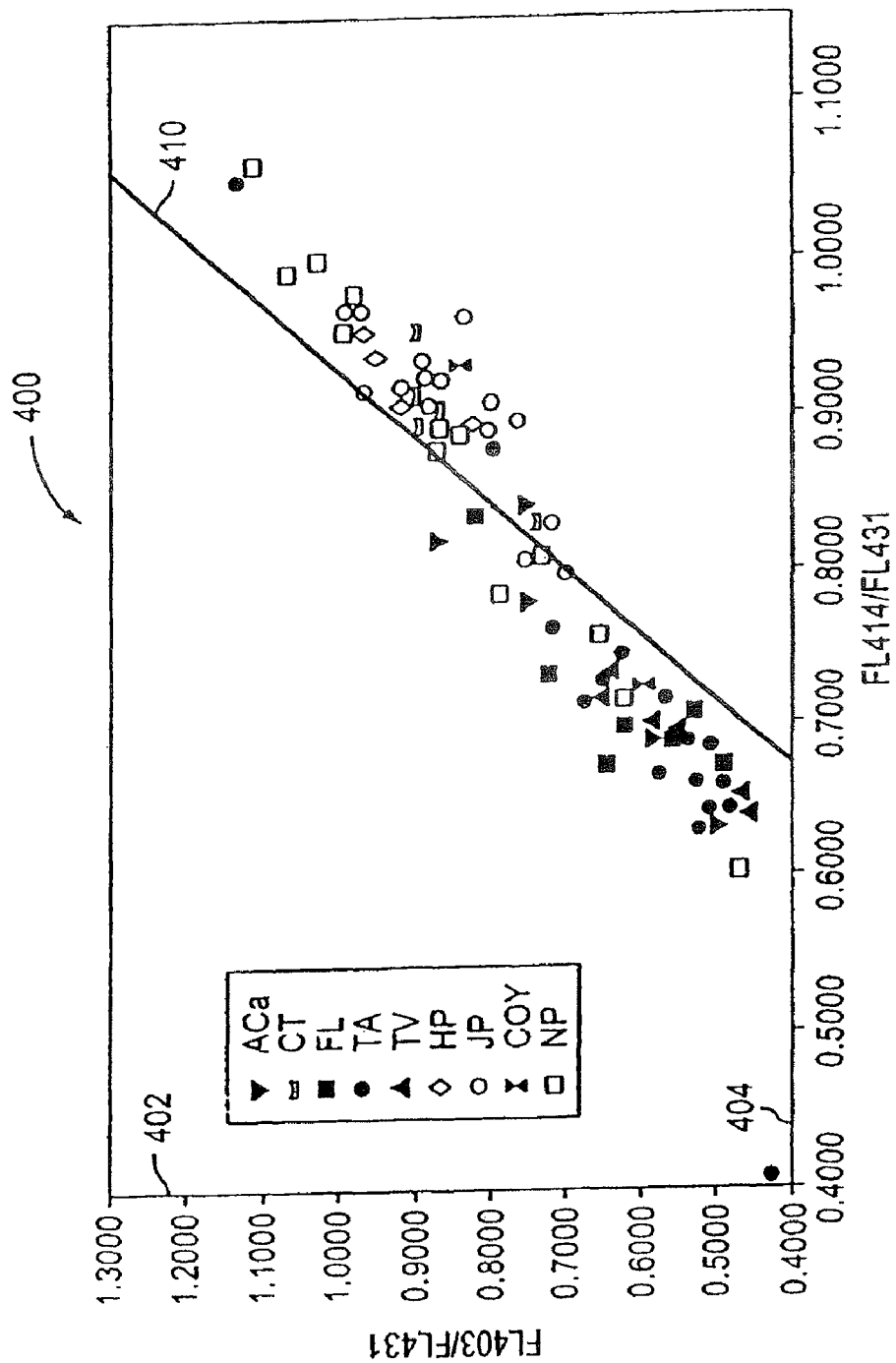
FIG. 4 is a graph showing polyp classification results obtained using a linear discriminant analysis according to principles of the invention.

FIG. 4 is a graph 400 showing illustrative polyp classification results obtained using a linear discriminant analysis for the colonic polyp example discussed above. One hundred and fifty patients were enrolled in a prospective study in which 94 polyps were collected from 50 patients. In FIG. 4, the about 403 nm to about 431 nm fluorescence intensity ratio ($I_{403}/I_{431}$) was plotted along the vertical axis 402 against the about 414 nm to about 431 nm ratio ($I_{414}/I_{431}$) plotted along the horizontal axis 404 for a given polyp. The LDA threshold discrimination model is depicted as the line 410 in FIG. 4 where polyps corresponding to data points that lie above the line 410 are classified as neoplastic polyps and polyps corresponding to data points that lie below the line 410 are classified as non-neoplastic polyps. Using this model, 47 of 52 neoplastic polyps and 34 of 42 non-neoplastic polyps were classified correctly resulting in a sensitivity and specificity of 90% and 81%, respectively. In addition, 80 of 86 normal colonic tissue sites and 3 of 3 frank adenocarcinomas were correctly classified.

OTHER EXAMPLES

The apparatus of FIG. 1 is used in other exemplary systems and methods of the invention. Specimens to be tested for diagnostic purposes are illuminated with excitation radiation, such as 337 nm illumination. Intensities of fluorescent responses at first and second wavelengths are observed, and are normalized using an intensity of a response at an isosbestic point. In preferred embodiments, the isosbestic point occurs at 431 nm. The normalized intensities are analyzed by comparison to a discrimination function.

Various linear or non-linear discriminant functions can be devised using the complex relationship between tissue fluorescence measured on the surface and the distribution of different fluorophores that exist in different tissue layers. The analysis is further complicated by primary absorption of the excitation light and secondary absorption of the emitted light at different wavelengths by the same fluorophores and other chromophores as the light used for excitation and the emitted light propagate through scattering media such as tissue. Diagnostic systems and methods of the invention will operate according to a non-linear discriminant when an excess and/or a deficit of one or more of such substances is indicative of a condition of health.

Diagnostic systems and methods of the invention will operate according to a non-linear discriminant based on other factors as well. For example, in the field of colposcopy, non-linear discriminants can vary with other factors such as the age or race of the patient or whether the patient is pre-, peri- or post-menopausal.

Potential Cost Savings

The ability to identify and distinguish benign and malignant polyps in situ could result in substantial cost savings. In this particular example, 39 of 94 polyps would have been spared from being resected and biopsied, representing a 41% savings in surgical and pathology charges. However, at present there is a false negative rate of 9.6%. The long term outcome of not resecting these polyps will need to be determined. In comparison, other techniques spared 14% of the polyps from being biopsied and had a false negative rate of 0.9%. If polyps greater than 5 mm in the latter study are excluded from this analysis, then 27% of the polyps would not have been biopsied and the technique would have a 3.2% false negative rate.

Application to Other Tissues

The systems and methods of the invention have been described with regard to observations on colonic tissue. The invention, involving a new probe design and analytical method, can enhance the accuracy for identifying neoplasia in other tissues such as the cervix of the uterus, the esophagus, the urinary bladder, the oral cavity, and the bronchotracheal tree.

Equivalents

While the invention has been particularly shown and described with reference to specific preferred embodiments, it should be understood by those skilled in the art that various changes in form and detail may be made therein without departing from the spirit and scope of the invention.

What is claimed is:

1. A system for determining a condition of a colon tissue, the system comprising:
   an illumination source configured to illuminate the colon tissue with a predetermined excitation wavelength;
   a detector configured to:
      receive light that is emitted from the colon tissue in response to the illuminating of the colon tissue; and
      output emitted intensity data that includes a plurality of emitted intensity values corresponding to wavelengths of the received light; and
   a computational module configured to:
      determine, using the emitted intensity data, an isosbestic wavelength;
      normalize, using an intensity associated with the isosbestic wavelength, the plurality of emitted intensity values;
      perform an analysis of a plurality of the normalized emitted intensity values; and
      generate, based on the analysis, an output characterizing the condition of the colon tissue.

2. The system of claim 1, wherein the predetermined wavelength is 337 nano-meters (nm).

3. The system of claim 1, wherein the colon tissue includes a portion of a colon polyp.

4. The system of claim 1, further comprising:
   a fiber optic path for conducting light from the illumination source to the colon tissue, the conducting light being associated with the predetermined excitation wavelength.

5. The system of claim 1, further comprising:
   a fiber optic path for conducting the received light from the colon tissue to the detector.

6. The system of claim 1, wherein the normalizing is based on one emitted intensity value of the plurality of emitted intensity values.

7. The system of claim 1, wherein the analysis is a linear discrimination analysis.

8. The system of claim 1, wherein the generated output indicates whether the colon tissue is likely to be neoplastic.

9. A method comprising:
   illuminating a tissue with a first excitation wavelength;
   obtaining light from the tissue, the light comprising a plurality of wavelengths, the plurality of wavelengths corresponding to a plurality of intensity values;
   determining an isosbestic wavelength associated with the plurality of wavelengths, the isosbestic wavelength associated with a first intensity value;
   normalizing, using the first intensity value, the plurality of intensity values; and
   perform an analysis of the normalized intensity values to determine an output characterizing a condition of the tissue.

10. The system of claim 9, wherein the first wavelength is 337 nanometers.

11. The system of claim 10, wherein the isosbestic wavelength is 431 nanometers.

12. The method of claim 9, wherein the normalizing is performed by dividing at least one intensity value of the plurality of intensity values by the first intensity value.

13. The method of claim 9, wherein the analysis is a linear discriminant analysis.

14. The method of claim 9, wherein the analysis is a non-linear analysis.

15. The method of claim 14, wherein:
the tissue is associated with a patient; and
the non-linear analysis varies based on an at least one of an age of the patient and a race of the patient.

16. The method of claim 15, wherein the non-linear analysis varies based on a menopause stage of the patient.

17. The method of claim 9, wherein the output comprises a score.

* * * * *